United States Patent [19]
Maltsev et al.

[11] Patent Number: 5,650,847
[45] Date of Patent: Jul. 22, 1997

[54] METHOD AND DEVICE FOR DETERMINATION OF PARAMETERS OF INDIVIDUAL MICROPARTICLES

[75] Inventors: Valeri Pavlovich Maltsev; Andrei Vitalievich Chernyshev, both of Novosibirsk, Russian Federation

[73] Assignee: Erkki SOINI, Kirjala, Finland

[21] Appl. No.: 490,454

[22] Filed: Jun. 14, 1995

[51] Int. Cl.$^6$ .................................................. G01N 15/02
[52] U.S. Cl. .......................................................... 356/336
[58] Field of Search .................................. 356/336, 128, 356/73, 337, 343

[56] References Cited

U.S. PATENT DOCUMENTS 4,286,876  9/1981  Hogg et al. ............................ 356/343

OTHER PUBLICATIONS

Maltsev et al., "Light Scattering and Fluorescence of Single Particles Measured by a Scanning Flow Cytometer", Int'l Symp. on Biomed. Optics, Paper No. 2386B-30, Session 5, San Jose, CA, Feb. 8, 1995 & Proceedings of SPIE, 2386 (1995) 199–205.

P.J. Wyatt, "Discrimination of Phytoplankton via Light-Scattering Properties", 34 *Limnology and Oceanography*, 96–112 (1989).

Maltsev et al., "Estimation of morphological characteristics of single particles from light scattering data in flow cytometry," Russian Chem. Bull. 43, 1181–1190 (Jul. 1984) (with English language abstract).

Phillips et al., "Measurement of the Lorenz–Mie Scattering of a Single Particle: polystyrene latex", *Colloid and Interface Science*, 1970, 34, p. 159.

P.J. Wyatt, "Light Scattering in the Microbial World", *Colloid and Interface Science*, 1972, v. 39, pp. 479–491.

V.R. Stull, "Size Distribution of Bacterial Cells," *J. Bacteriol.*, 1972, 109, pp. 1301–1303.

Wyatt et al., "Aerosol Particle Analyzer", *Applied Optics*, 1988 27 (2), pp. 217–221.

*Primary Examiner*—Frank G. Font
*Assistant Examiner*—Amanda Merlino
*Attorney, Agent, or Firm*—Adduci, Mastriani & Schaumberg, L.L.P.

[57] ABSTRACT

A method and device for determination of absolute values of the size and the refractive index of individual microparticles. An optical scanning device for measurement of angular scattering pattern from individual microparticles is described. The light scatter is measured in different angles from moving particles inside the scanning optical system and the values and the angular locations of minima and maxima of the scattering pattern are registered. The size and the refractive index of individual microparticles are calculated from the registered minima and maxima using an empirical equation. An empirical equation has been derived from statistical analysis of angular scattering patterns. These patterns have been calculated on the basis of Mie scattering theory.

5 Claims, 10 Drawing Sheets

METHOD AND DEVICE FOR DETERMINATION OF PARAMETERS OF INDIVIDUAL MICROPARTICLES

This invention relates to a method and device for analysing morphological parameters of microparticles. The microparticles in this context mean organic, polymeric or inorganic microparticles or aerosols or small biological objects including cells, spores and other living or nonliving particles. The morphological parameters in this context mean the physical dimensions including minimum and maximum diameter and the optical refractive index. In particular, this invention provides a fast and absolute methodology for measuring the diameter and the refractive index of individual spherical particles with the size from 0.8 µm to 100 µm.

In fast analysis of large number of individual microparticles in absolute units, it is important to use a method that provides real-time data for determination of morphological parameters of microparticles including size and refractive index. This invention is particularly related to analysis of particles with light scattering. The method of the invention is called "Flying Light Scattering Indicatrix" by inventors and is referred to as "FLSI" in this text which means determination of the angular dependency of the intensity of light scattered by a moving individual particle. The term "Indicatrix" is equivalent with the term "Light Scattering Pattern", "LSP" commonly used in the literature and in this text. The device of this invention is called Scanning Flow Cytometer and later referred to as "SFC" is based on measurement of angular light scattering pattern, i.e. the intensity of the light scattered from individual microparticles as function of the scattering angle. The optical scanning system provides the measurement of the intensity of the light scattered in different polar angles from moving particles. The particle parameters are calculated from the registered LSP using an empirical equation. The empirical equation has been derived from statistical analysis of angular scattering patterns. These patterns have been calculated on the basis of Mie scattering theory for particle parameters varied in required regions of the size and the refractive index of the particle.

BACKGROUND OF THE INVENTION

The publications and other materials used herein to illuminate the background of the invention, and in particular, cases to provide additional details respecting the practice, are incorporated by reference.

Various light scattering methods have been used in scientific research and industrial technologies in order to determine the size distribution of particles. These methods can be divided into the following categories: 1) methods based on analysis of light scattered by a particle suspension; 2) methods based on analysis of light scattered by an individual particle. This invention is related to the latter category.

The instrumental set-up commonly known and used for flow cytometry can be applied to analysis of individual particles. The hydrofocusing system allows the measurement of scattering or/and fluorescence from individual particles with a speed varying from 10 up to 1000 particles per second. Several alternative design principles of hydrofocusing heads have been described in the literature for the purpose of measurement of various parameters from the light scattering. These methods have been reviewed by Salzman & al. in: Flow Cytometry and Sorting, Second Edition, M. R. Melamed, T. Lindmo, M. L Mendelsohn, Eds. Wiley & Sons, Inc., New York, 1990, pp. 81–107. The ordinary flow cytometer, however, does not allow absolute determination of particle parameters with the accuracy and precision required by the applications of this invention. In the ordinary flow cytometer the laser beam is focused perpendicular to the flow of particles and it measures the light scattering from microparticles in one fixed polar angle only and is not applicable for the measurement of the entire scattering pattern.

It is important to measure the entire scattering pattern for individual particles, because the angular scattering pattern completely characterises properties of the particle. In investigation of morphological characteristics of particles (size, refractive index, shape, etc.), scattering pattern works like a finger-print. Various parameters including angular locations of maxima and minima, maxima to minima ratios etc. can be determined from the angular scattering pattern and used for calculation of the morphological parameters.

In following we review the methodology known in the literature applicable for measurement of the morphological parameters as referred to above.

An empirical solution for the inverse-scattering problem of individual particles is provided by the optical strip-map technique introduced by G. M. Quist and P. J. Wyatt, (Empirical solution to the inverse-scattering problem by the optical strip-map technique, J. Opt. Soc. Am. A2, pp. 1979–1986 (1985)). This technique allows the determination of particle parameters from analysis of the intensity of the light scattered in fixed angles.

The volume distribution of red blood cells was determined by D. H. Tysko, M. H. Metz, E. A. Epstein, A. Grinbaum, "Flowcytometric light scattering measurement of red blood cell volume and haemoglobin concentration", Appl. Opt. 24, 1355–1365 (1985)). as they measured the light scattered into two angular intervals. Two photo diodes detected the scattering light collimated at polar angles from 2.5° to 5° and from 6° to 9°, and at azimuthal angles from 0° to 360° for both detectors. Drops of heptane, nonane, and dodecane in water was used for calibration.

The Mie scattering model of marine particles was developed and tested by S. G. Ackleson and R. W. Spinard (Size and refractive index of individual marine particulates: a flow cytometric approach, Appl. Opt. 27, 1270–1277 (1988)), who used a conventional flow cytometer and well-defined polystyrene particles. The model was used for simultaneous measurements of near-forward light scatter and side scatter that yielded particle sizes within the range of d=1–10 µm and refractive indexes within the range of n=1.35–1.47. The size distribution of marine particles in clear ocean waters was analyzed.

Milk fat and latex particle size distributions were analyzed by K. Takeda, Y. Ito, and C. Munakata (Simultaneous measurement of size and refractive index of a fine particle in flowing liquid, Meas. Sci. Technol. 3, 27–32 (1992)). In this study, light intensities at two different wavelengths (441.6 and 632.8 nm) and scattering in both forward and sideways directions were measured. In order to determine rapidly the size and the refractive index of any given particle, the inverse problem of Mie scattering was solved using the optical strip-map technique.

Relation of particle sizes and refractive indices to locations of minima was investigated by M. Kerker (In: The Scattering of Light and Other Electromagnetic Radiation. Academic, New York, 1969) and H. C. van de Hulst (In: Light Scattering by Small Particles, Wiley, New York, 1957). However, determining of particle parameters from the scattering data (an inverse problem of scattering) still remained as a vital problem.

An approach for the measurement of the scattering utilizing the motion of a particle in the flow of carrier liquid was described by Loken et al. (Cell discrimination by multiangle light scattering, Histochem. Cytochem. 24, 1976, 284–291).

An optical system recorded the scattering intensity versus time, which expresses the intensity of single particle scattering versus scattering angle for polar angles from 1.0° to 49.0°. To correct the measured scattering function for variations of the illumination intensity and for collection aperture as a function of particle position, the transfer function was determined empirically by introducing fluorescent particles into the flow.

Ludlow and Kaye (A scanning diffractometer for the rapid analysis of microparticles and biological cells, Colloid Interface Sci. 69, 1979, 571–589) used a scanning diffractometer with a single photomultiplier to measure the scattering of polystyrene particles and spores. A rotating disk and 174 optical light-guides allowed the measurement of scattering intensities of single particles at polar angles from 3° to 177° in 2.8 ms. The size distributions and mean refractive indices were determined by comparison with the Mie scattering characteristics for homogeneous spheres.

A differential light scattering photometer described by Bartholdi et al. (Differential light scattering photometer for rapid analysis of single particles in flow, Applied Optics 19, 1573–1584 (1980)) allows momentary measurement of scattering from single particles. A ellipsoidal reflector reflects emitted scattering in polar angles from 2.5° to 177.5° and azimuthal angles from 0° to 360° onto a circular array of 60 photo diodes. This optical system performs fast measurement of the light scattering and fast analysis of single particles.

OBJECT OF THE INVENTION

An object of this invention is to provide an improved method called FSLI for measuring morphological particle parameters of individual particles from light scattering pattern (LSP). FSLI method and SFC device has been introduced by the inventors (V. P. Maltsev, Estimation of morphological characteristics of single particles from light scattering data in flow cytometry, Russian Chemical Bulletin 43, 1115–1124, July 1994) and the method can be used to measure size distributions for example of the latex (polystyrene), milk fat, spore particles. FLSI method using SFC and related empirical equations provides absolute sizing of microparticles at the rate of a minimum 50 particles per second. The size distribution obtained by both the FLSI method and best-fit procedure using Mie Scattering theory will be compared in this patent description.

BRIEF DESCRIPTION OF THE FIGURES

FIG. 6 shows the scattering intensity versus scattering angle for latex particles using a) green laser and b) red laser. Points=experimental data; line=best-fit function calculated from the Mie theory.

FIG. 8 shows the scattering intensity versus scattering angle for a) *Penicillium levitum* spores; b) *Aspergillus pseudoglaucus* spores and c) milk fat particles. Points= experimental data; line=best-fit function calculated from the Mie theory.

FIG. 9 shows the size distribution of *Penicillium levitum* spores a) calculated according to the invention and b) calculated according to the Mie theory.

FIG. 10 shows the size distribution of *Aspergillus pseudoglaucus* spores a) calculated according to the invention and b) calculated according to the Mie theory.

FIG. 11 shows the size distribution of milk fat particles a) calculated according to the invention and b) calculated according to the Mie theory.

DETAILED DESCRIPTION OF THE PREFERRED EMBODIMENTS

Figure 1:
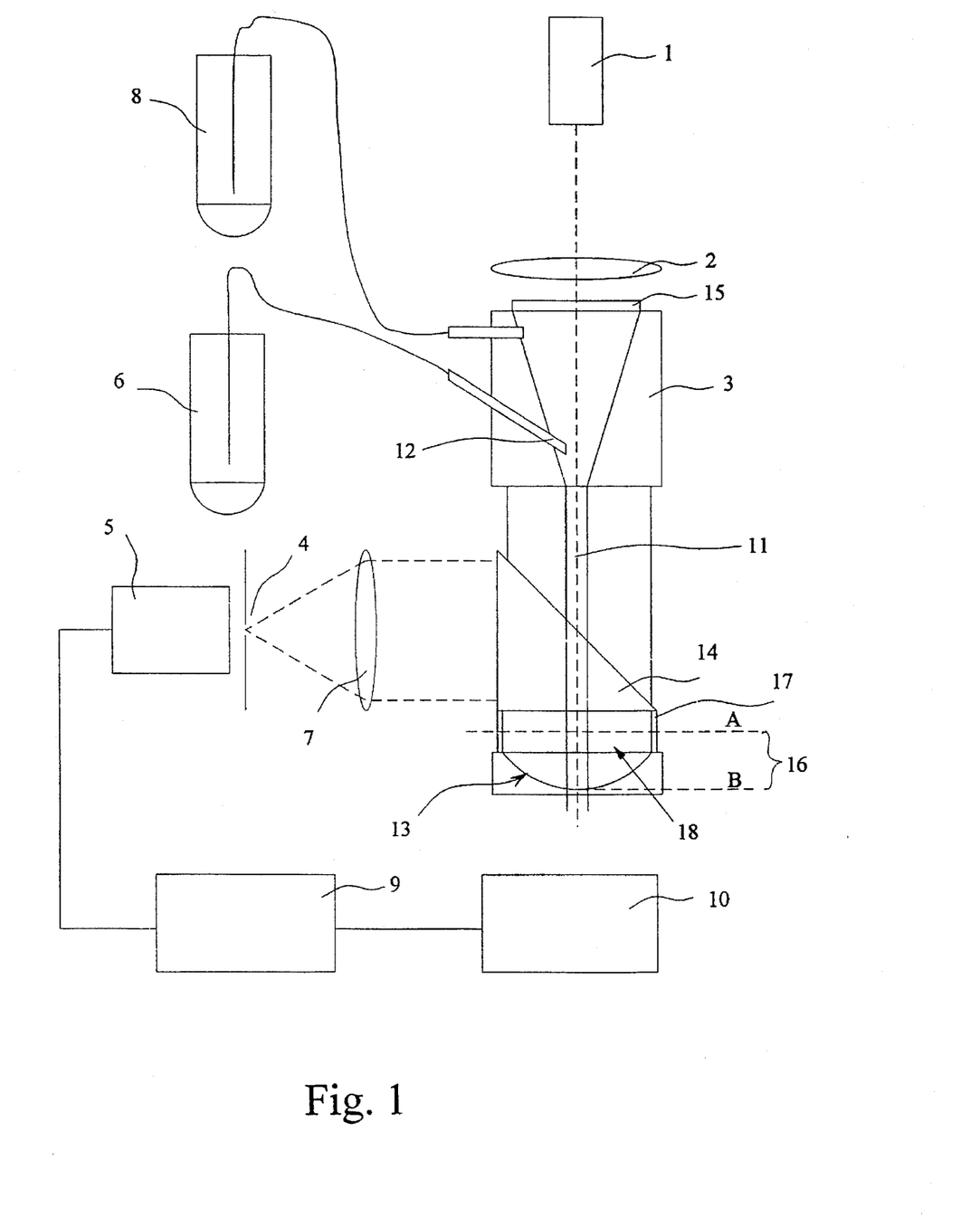
FIG. 1 is a schematic diagram of the optical and hydrofocusing system according to the invention.

The schematic diagram of the optical and hydrofocusing system according to this invention is shown in FIG. 1. The system consists of a laser (1), laser beam focus lens (2), hydrofocusing head (3), pin hole (4), photodetector (5), pressurised sample container (6), lens (7), pressurised sheath liquid container (8), electronics including an amplifier and an AD-converter (9) and a computer (10). The optical cuvette incorporates following parts: capillary flow channel (11), sample liquid injector (12), spherical reflector (13), plane reflector (14), optical window (15) and testing zone (16).

The hydrofocusing head (3) produces two concentric streams: an internal stream (diameter 10 μm) carrying the tested particles and an external sheath-stream. A differential pressure system controlling the pressure in the containers (6) and (8) provides a precise flow velocity up to 1 m/s for the internal stream. A 12 mW He-Ne laser or any other continuous wave green-red region laser (1) can be used to illuminate particles in the testing zone (16). The special feature if compared with an ordinary flow cytometer is the arrangement of laser illumination of particles in the flow. The laser is focussed coaxially to the capillary flow channel (11) inside the hydrofocusing head. The particle motion is coaxial with the incident laser beam (diameter 30 μm) resulting in uniform illumination over the test zone (16) and over a wide range of scattering angles.

An example of a possible practical design of the hydrofocusing head (3) incorporates an optical window (15) for the laser beam which is directed coaxially into the optical cuvette. The lens (2) (focal length 70 mm) produces a 3 mm long test zone (16) inside the optical cuvette with uniform illumination of the internal stream. Another lens (7) (focal length e.g. 16 cm) focuses the scattering light leaving the optical cuvette into a 200 μm pin-hole (4) at 10 mm distance from a photodetector (5) (a diode or a photomultiplier tube). Due to the 10 mm distance only those photons which are parallel before the lens (2) will be detected and the stray light is rejected. The flow produced by the hydrofocusing head is directed into a capillary (11) with internal diameter 0.2–0.6 mm, made e.g. quartz and thus having a refractive index of 1.458 which is mounted inside a prism (14), a quartz cylinder ring (17) and a spherical reflector (13) (radius e.g. 5.0 mm). The interspace (18) between prism, cylinder ring and spherical reflector is filled with immersion liquid (glycerol, refractive index 1.473). It is obvious that the construction of the hydrofocusing head can be made of many alternative materials and designs.

Figure 2:
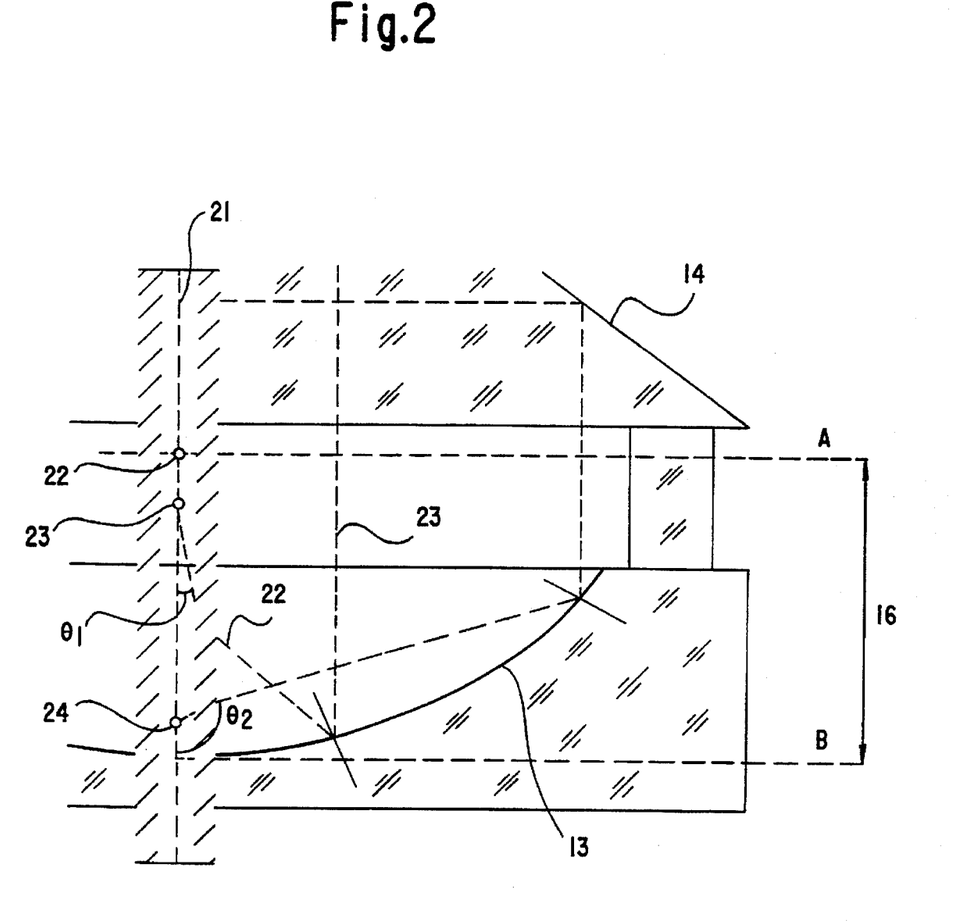
FIG. 2 illustrates the function of the optical cuvette.

FIG. 2 shows more accurately the function of the optical cuvette. The laser beam (21) and scattered rays (22) and (23) are shown in dashed lines. For every particle position within the illuminated test zone (16), the light scattered only at a specified angle θ will be reflected in parallel with the stream by the spherical reflector (13). When the particle is passing the point (23) the scatter light at the angle $\theta_1$ from the particle activates the detector. The angle θ varies continuously from $\theta_1$ to $\theta_2$ as the particle moves from the point (23) to the point (24) within the testing zone of the optical cuvette. The parallel rays reflected by the prism surface (14) leave the optical cuvette and are focused by a lens into a pin-hole in front of the photomultiplier. The signal as function of time is directly related to scattered light intensity versus scattering angle. The essential features of the device of this invention are, first, the spherical reflector (13) and the coaxial flow and illumination along the axis of this spherical reflector (11), second, the plane reflector (14) and the lens (7) which focus the parallel rays from the spherical reflector to the pinhole (4) of the photodetector (5).

Figure 3:
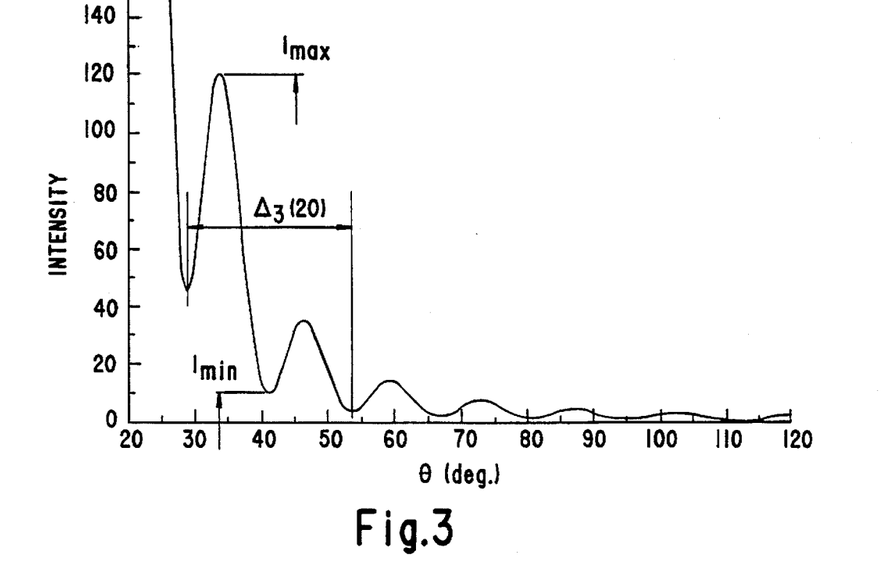
FIG. 3 shows the scattering intensity of a typical signal versus scattering angle.
Figure 4:
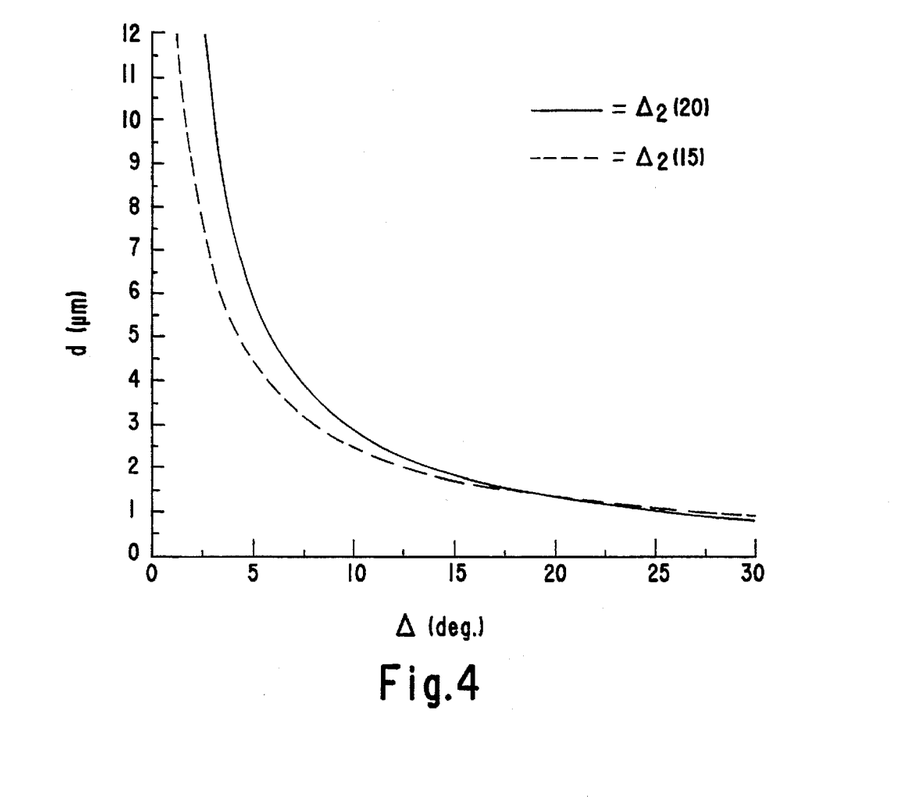
FIG. 4 shows the relationship between particle diameter and the distance (in degrees) between the first and the second scattering intensity minimum for boundary angles 20° and 15°, respectively.

This optical system allows measurement of the LSP of individual particles in polar angles θ from 10° to 120°. FIG. 3 shows the intensity of a typical signal versus scattering angle θ. (The angle θ is presented in time units in the optical detection system of SFC.) LSP-parameter $\Delta_2$ (BA) is the distance in degrees between the 1st and 2nd minima that occur after the boundary angle BA. The boundary angle (BA) is the lower limit of the scatter measurement angle θ. The LSP-parameters shall be measured at scattering angles larger than the BA. The distance between the first and second minima $\Delta_2$ (BA) is dependent on the particle size d and this relationship is shown in FIG. 4 where the dotted line shows the particle size (diameter μm) as function of $\Delta_2$ (15) and the solid line as function of $\Delta_2$ (20). The size of homogeneous, nonabsorbing spherical particles can be calculated from the distance using an empirical equation.

Another signal which is necessary for determination of the refractive index and which can be calculated from the light scattering pattern, is the "visibility" V. Visibility is defined as $V=(I_{max}-I_{min})/(I_{max}+I_{min})$, where $I_{max}$ is the scattering intensity at the angle of the next maximum after the boundary angle and $I_{min}$ is the scattering intensity at the angle of the next minimum after the boundary angle (see FIG. 3). The refractive index of homogeneous, nonabsorbing spherical particles can be calculated from the LSP-parameter $\Delta_2$ (BA) and visibility V using an empirical equation as shown later.

For analysing the signal from the photodetector and for fast calculation of the microparticle parameters, an appropriate amplifier and an analog-to-digital converter and a signal processor and a computer is needed. For triggering the electronics and signal processing, it is convenient to use a separate trigger laser beam which can be located for example at level A in FIGS. 1 and 2. The system described above can incorporate also an automatic real time flow speed measuring device which is based for example on the use of two laser beams at certain distance from each other and two forward scattering detectors and a time measuring device. It eliminates the need for precise speed control and permits the system to operate at variable flow speed.

The dependence of collection efficiency on particle position—the transfer function—is needed for the purpose of calibration of scattering collection efficiency. The transfer function which shows the transfer coefficient and the scattering angle as function of particle location (distance from the spherical reflector bottom=level B in FIGS. 1 and 2) was calculated on the basis of the real geometrical dimensions of the optical system. A plot of the photodetector signal versus time can thus be directly related to the scattered light intensity versus the scattering angle.

Figure 5:
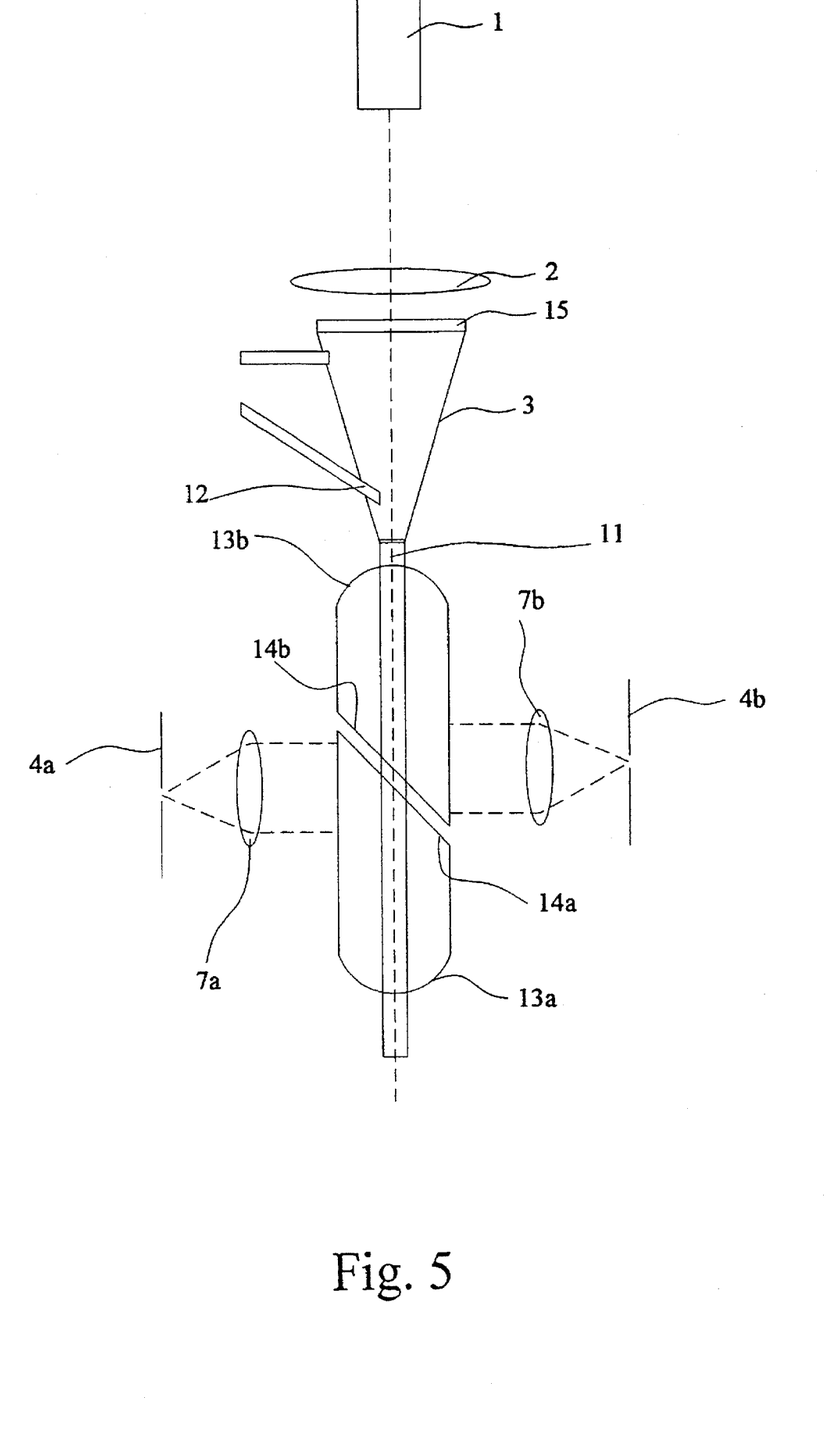
FIG. 5 shows an optical cuvette for measurement of light scattering pattern in polar angles ranging from 10° to 170°.

FIG. 5 shows the optical layout of an optical cuvette for measurement of the LSP of individual particles in polar angles θ from 10° to 170°. The reference numbering in this figure are same as in FIGS. 1 and 2. This optical cuvette incorporates two spherical reflectors (13a) and (13b) and two plane reflectors (14a) and (14b) opposite to each other with the flow channel (11) in line with the optical axis of the spherical reflectors. The upper pair of reflectors focus the light scattered in large angles 90°–170° to the pinhole and the lower pair of reflectors focus the light scattered in small angles 10°–90° to the pinhole. Using this optical layout both forward scattering and back scattering patterns can be registered. This is useful for extracting more complete morphological information for the microparticles from LSP's.

The method and device according to this invention provides many advantages if compared with the methods and devices known in the literature.

The pin-hole diameter (200 μm) of the device of this invention provides angular resolution of about 0.1°. The optical system of this invention allows measurement of LSP for very wide range of polar angles from 5° to 120°. For every polar angle, the collection optics integrates over very wide range of azimuthal scattering angles from 0° to 360°. For every polar angle, the collection optics integrates over the range of azimuthal scattering angles from 0° to 360°. The particle motion is coaxial with the laser beam resulting uniform illumination.

In the following discussion, the advantages of this invention are related in more detail to methods and devices published earlier:

In the paper published by Bartoldi & al. the angular resolution was about 2.5° and it is not useful for the measurement of location of minima and maxima of particles with size more then 10 μm as the distance between minima is smaller than the angular resolution of the optical system. As a consequence of the insufficient angular resolution the determination of maximum and minimum points is not accurate enough and then the accuracy of particle parameter calculations is reduced. Second, the use of an array of photodiodes with different characteristics requires calibration using particles with known parameters. Third, as manufacturing of an ellipsoidal reflector is not a simple process then the quality of the reflector surface as well as the profile and reflection parameter have to be carefully controlled.

The device described by Ludlow & al. employs a scanning diffractometer consisting of 174 optical light guides with limited angular resolution in the order of a few degrees. The optical differences between the light guides lead to the need of calibration and control procedures. The scanning diffractometer does not provide azimuthal scattering integration and it leads to a low sensitivity of scattering intensity measurement and narrow size range of particles to be analyzed. For uniform illumination of particles during the scattering measurement, the system requires lower flow speed that results in low rate of particle analysis.

The optical system of the flow cytometer described by Loken & al. does not provide integration of the azimuthal scattering angles that leads to low sensitivity of scattering measurement and narrow region of particles to be analyzed. The perpendicular configuration of flow and laser beam does not provide uniform illumination of particles during scatter measurement. The narrow angular region for scatter measurement (1°–49°) limits the applicability of this device.

The equations referred to in the following are shown in Scheme 1.

Empirical Equations

Empirical equations used with the FLSI method allow determination of particle size and refractive index from measured LSP [A. V. Chernyshev & al., Measurement of scattering properties of individual particles using a scanning flow cytometer, accepted by Applied Optics for publication]. The empirical equations have the general form $$y = p_0 + p_1 x^{-1} + p_2 x^{-2} + p_3 x^{-3} \ldots p_n x^{-n}$$

where y=refractive index or diameter of the particle, $P_i$=coefficient and x=LSP-parameter $\Delta_2$ (BA) or visibility V.

In order to produce the required empirical equations, we computed extremum intensities and their angular locations according to Mie scattering theory using a program proposed by C. F. Bohren and D. R. Huffman (Absorption and scattering of light by small particles, Wiley, New York, 1983, Appendix A, p. 609). Calculations were made for a set of nonabsorbing particles with particle size d from 1 μm to 12 μm with a step of 0.1 μm and particle refractive index n from 1.37 to 1.60 with a step of 0.01. In addition we assumed unpolarized incident light with wavelengths λ=0.6328 μm and the optical medium refractive index $n_0$=1.333.

In order to obtain an empirical equation that relates LSP parameter to particle size, a non-linear fitting procedure was applied both to the initial particle size and the size calculated from the tested equations. An empirical equation can be obtained from the minimization of the parameter residual standard error. Empirical equations for refractive index can be obtained in similar way.

We produced the first Equation 1 for the following regions of particle parameters: the size between 1 μm and 12 μm and the refractive index between 1.55 and 1.60. For these regions, we used the LSP parameter $\Delta_2$ (20) which was computed from the above-mentioned LSP set. In Equation 1 $p_1$=−0.158 (s.d.=0.017), $p_2$=30.13 (s.d.=0.12), $p_3$=2.3 (s.d.=0.7). This function is shown in FIG. 4 where the solid line shows particle size as a function of difference between the 1st and 2nd minima that occur after the boundary angle of 20° for latex particles. Equation 1 yields a residual standard error of 0.10 μm for particle sizes within the above-mentioned size ranges and refractive indices (incident light at wavelength of 0.6328 μm and medium refractive index of 1.333).

An analogous method was used in order to produce an equation for the size applicable to the particles with sizes and refractive indices ranging from 1 μm to 12 μm and from 1.37 to 1.47, respectively. These regions correspond to biological particles and milk fat particles. In Equation 2 with LSP parameter $\Delta_2$ (15) $p_1$=0.080 (s.d.=0.014), $p_2$=26.86 (s.d.=0.10), $p_3$=200 (s.d.=20), and $p_4$=−420 (s.d.=40). This function is shown in FIG. 4 where the dashed line shows particle size as a function of difference between the 1st and 2nd minima that occur after the boundary angle of 15° for spores and milk fat particles. Equation 2 yields a residual standard error of 0.12 μm for particle sizes within the particle size ranges and refractive indices presented above. We used Equation 1 for latex particle sizing and Equation 2 for sizing of spores and milk fat particles.

An analogous method can be used in order to produce an equation for refractive index.

Determining of microparticle size by direct comparison of the theoretical and experimental LSP.

In following methods the experimental light scattering pattern of the microparticle sample will be compared with the theoretical LSP's which have been calculated for all different particle sizes and refractive indexes with sufficiently small steps. For simplicity reasons the methods are presented in following for determination of the size only but the method for the refractive index is analogous. For understanding the mathematical terminology and methodology used in following we refer to following textbooks: 1) S. Lipschutz, Theory and problems of linear algebra, Schaum's outline series, McGraw-Hill Book Co. 1968, 2) T. W. Anderson & al., A bibliography of multivariate statistical analysis, Edinburgh, 1973.

Direct comparison can be done by for example using dot product, simple correlation, Pearson's correlation or neural network methods. For this purpose LSP vectors, vectors of intensity values have to be determined. The experimental LSP vector is made by sampling the measured intensity values into a vector at discrete time intervals Δt by using the AD-converter. The theoretical LSP vector is made by calculating theoretical scattering intensity values by using algorithm proposed by C. F. Bohren and D. R. Huffman referred to above. The theoretical intensity function of angle θ is converted to function of time, where the time co-ordinate matches with the ratio of time/angle (t/θ) of the SFC system. The intensity values are calculated from this converted function at same discrete time intervals as in the experimental LSP vector and the intensity values are stored as a theoretical LSP vector. Different theoretical LSPs are calculated for a set of different particle sizes with sufficiently small steps. Selected step size will determine the resolution of size determination.

1) Dot Product Method

At first, theoretical LSP vectors $T_1, T_2, \ldots, T_n$ and their norms $\|T_1\|, \ldots, \|T_2\|, \ldots, \|T_n\|$ are calculated. Normalised LSP vectors are written into matrix form as shown by Equation 3. Dot product vector consisting dot products of each theoretical LSP vector and experimental LSP M can be obtained by calculation using Equation 4, 5 and 6, where P is a vector of dot products. In dot product vector P the index i of the maximum value of $P_1, P_2, \ldots, P_n$ indicates which theoretical LSP vector $T_i$ has a closest relation to the experimental LSP vector. When the particle size of each theoretical LSP vector $T_i$ is known, the size of measured particle can be determined.

2) Simple Correlation Method

In simple correlation method sum over squares of vector element differences is calculated. Let's assume that T represents the matrix of theoretically calculated LSP's. The vectors $T_i$ represent theoretical LSP vectors for different particle sizes. Simple correlation between experimental LSP vector and theoretical LSP vectors is defined by Equations 7 and 8. In opposite to dot product method the index i of the minimum value of vector v indicates which theoretical LSP vector $T_i$ has closest relation to the experimental LSP vector M.

3) Pearson's Correlation Method

Pearson's correlation method is closely related to the dot product and simple correlation method. However instead of using the dot product formula (4) or the simple correlation formula, the Pearson's correlation coefficient vector p is calculated from Equation 9 and 10 where $S_{Ti}$ is the standard deviation of the theoretical LSP vector $T_i$, and $S_M$ is the standard deviation of the experimental LSP vector, and $S_{TiM}^2$ is the covariance of vectors $T_i$ and M. Exactly as was done in the dot product method, the index i of the maximum correlation coefficient $\rho_i$ is found. Sphere size is the same as used in the calculation of $T_i$.

4) Neural Network Method

Multi layer perceptron neural networks provide an easy and fast way no determine the size of a measured particle (B. Kosko (1992), Neural networks and fuzzy systems. A dynamical systems approach to machine intelligence. Englewood Cliffs, N.J., U.S.A.: Prentice-Hall International Inc.). Similarly to the dot product and correlation methods, a set of theoretical LSP vectors $T_i$ for the desired range of particle size must be calculated in advance. Each theoretical LSP vector $T_i$ is assigned a desired value for neural network output $O_i$. The output value could for example be the size of the particle. The neural network is taught to recognise different theoretical scattering vectors and to produce a correct output for them. The teaching process can be done by using the Backpropagation algorithm (Kosko, 1992).

There are many possibilities for the structure of network. The number of input nodes should be same as the length of the LSP vector. Each vector element $M_j$ of a LSP vector M is fed into a corresponding input $I_j$ of the neural net. The neural net calculates the output according to the chosen weight functions and coefficients which have been taught to it during the training period. Many different weight functions for links between nodes of neural net can be used. For example linear or sigmoidal weight functions may be used. An advantage of using neural network is that it can be taught to be immune to the phase errors of the scattering pattern signal.

Examples of Measurement of Latex Particles

Latex particles are well-suited for determination of the accuracy of this method as standard latex particle suspensions consist of particles with well-known mean size and standard deviation. In our experiments, we have used polystyrene latex particles (Carboxylated Polystyrene Uniform Latex Microspheres, Duke Scientific, Cat.No. C300A) with mean size of 3.06 µm and standard deviation of 0.18 µm as specified by the manufacturer.

Figure 6A:
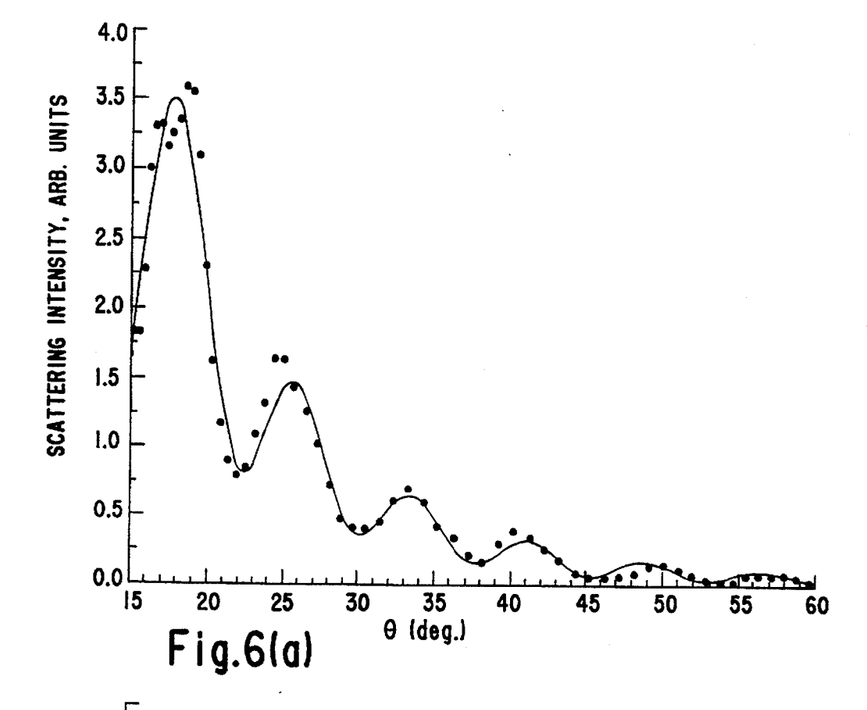
Figure 6B:
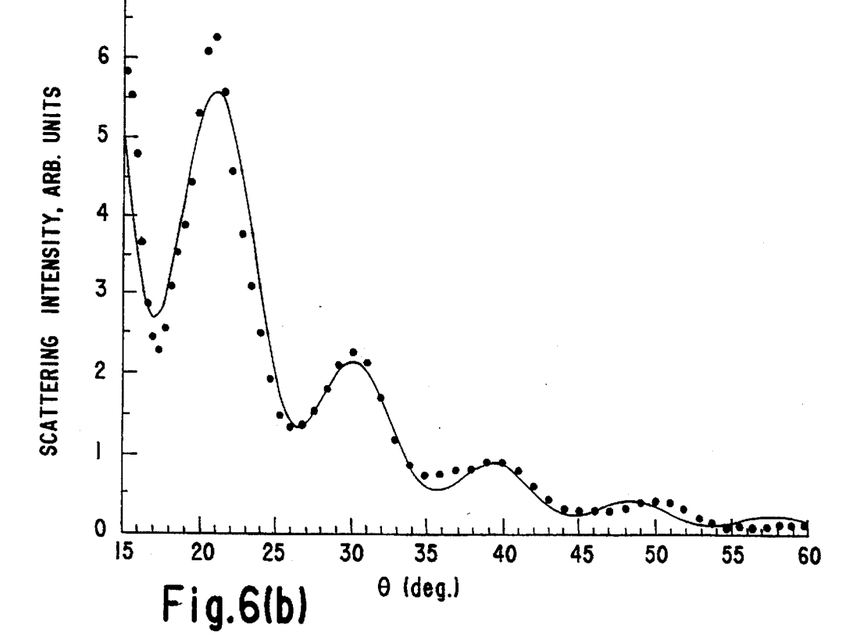

We have measured the LSP of Duke's latex particles at polar angles from 20° to 50°. The LSP of one measured particle using a green ($\lambda$=0.532 µm) and red ($\lambda$=0.6328 µm) laser beam are presented in FIGS. 6a and 6b respectively where the solid points show the experimental LSP of one latex particle and the solid line shows the best-fit function calculated from the Mie theory for these experimental data. The best-fit function gives the following parameters for the particle: size d=3.10 and refractive indexes n=1.558 (green) and n=1.578.

Figure 7:
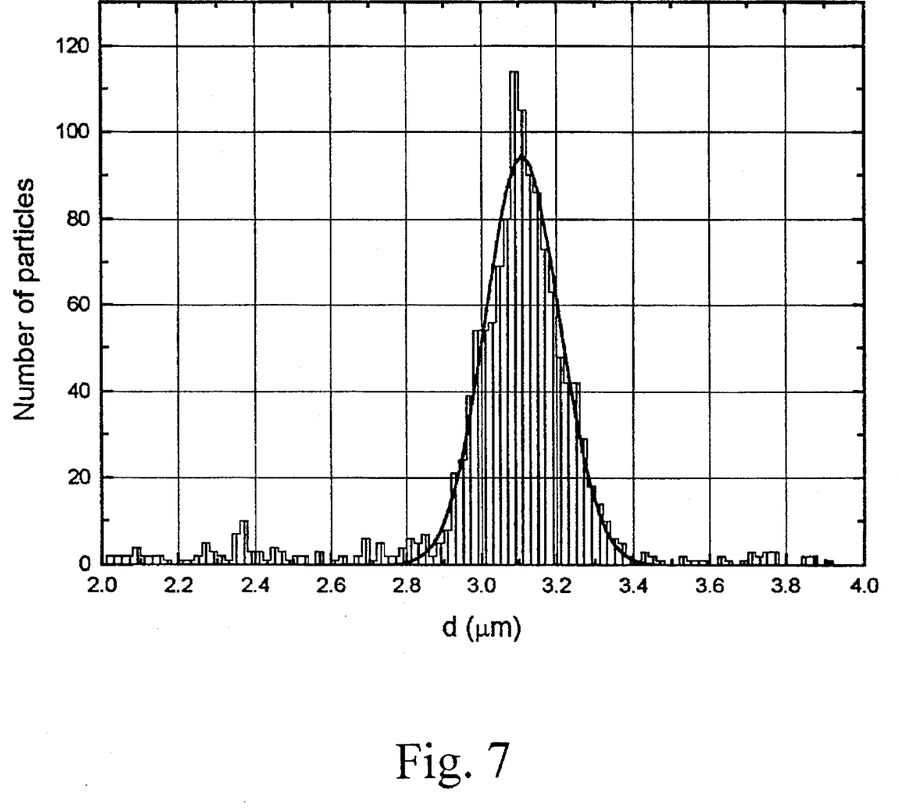
FIG. 7 shows the size distribution of 931 individual latex particles calculated according to the invention.

The size distribution produced by LSP's of 931 individual latex particles From Duke processed with the FLSI method is presented in FIG. 7. The parameters of the Gaussian size distribution that fall within the experimental size distribution are as follows: mean size of 3.11 µm and standard deviation of 0.19 µm.

An example of an application of the this invention is a multiparameter bioaffinity assay where latex microparticles are used as solid carrier of the reactants and the reaction suspension contains these particles in different categories relative to the diameter and the microparticles in each category are coated with different reactants specific to different analytes (T. M. McHugh & al.: Journal of Immunological Methods 95 (1986) 57–61 and pat. appl. no. EP-126 450). The fast and precise measurement of the diameter of microparticles of different categories is potential method for identification of the category of each microparticle. If the resolution of the the determination of the diameter is for example 0.25 µm, such multiparameter assay for 5 different simultaneous analytes would be based on the use of microparticles with following sizes: 5.0, 5.5, 6.0, 6.5, and 7.0 micrometers.

Examples of Measurement of Biological Particles

Figure 8A:
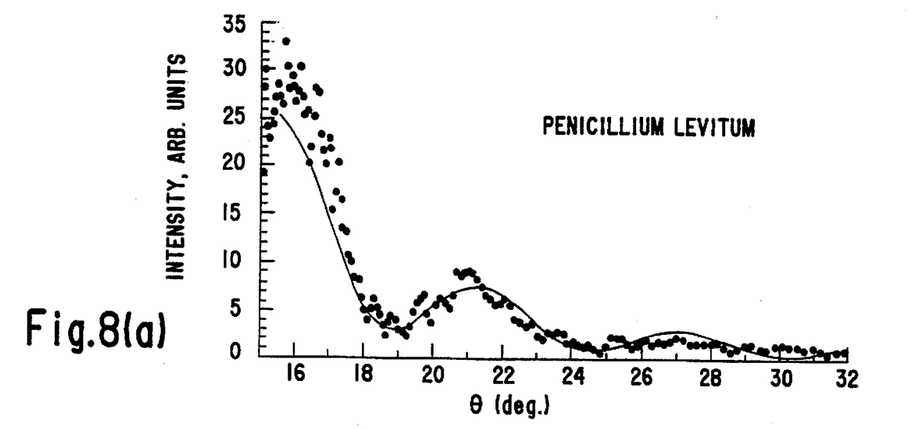
Figure 8B:
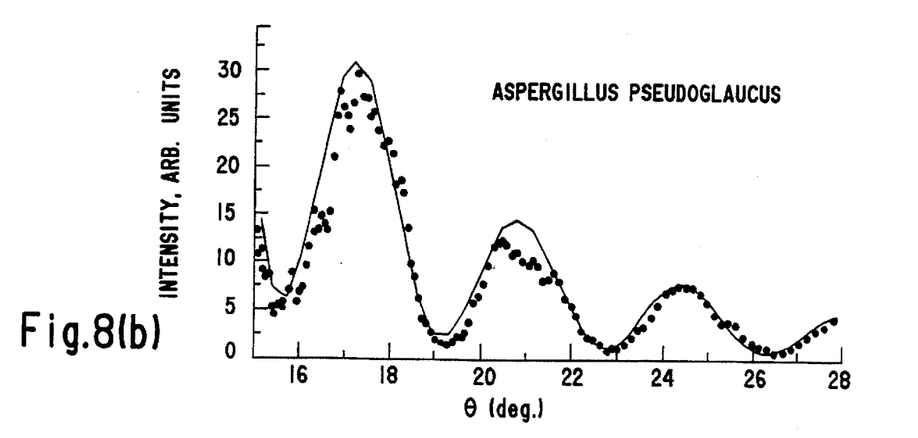
Figure 8C:
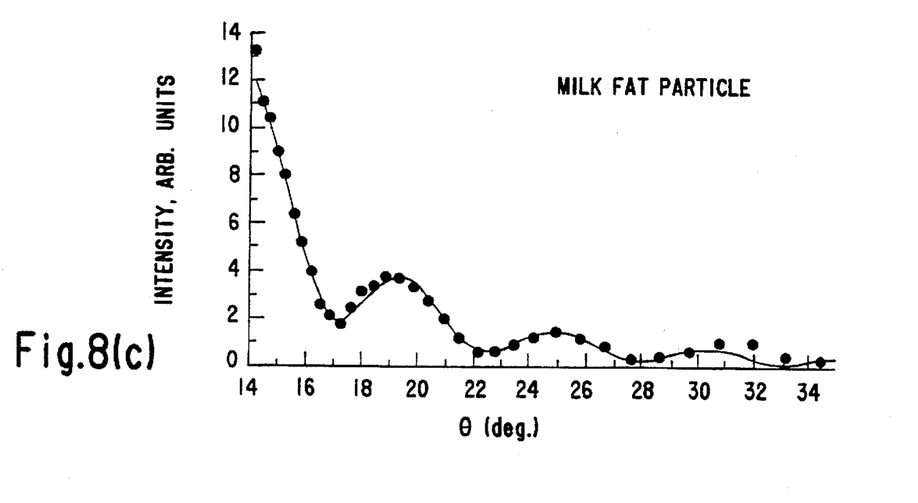

We have measured the size distribution of particles of unknown sizes. These include spores (*Penicillium levitum*, *Aspergillus pseudoglaucus*) and milk fat particles. LSP's obtained from these particles are shown in FIG. 8 where solid point shows the experimental LSP's of *Penicillium levitum* a) and *Aspergillus pseudoglaucus* spores b) and the solid line shows milk fat particle and best-fit functions calculated from Mie theory c).

Figure 9A:
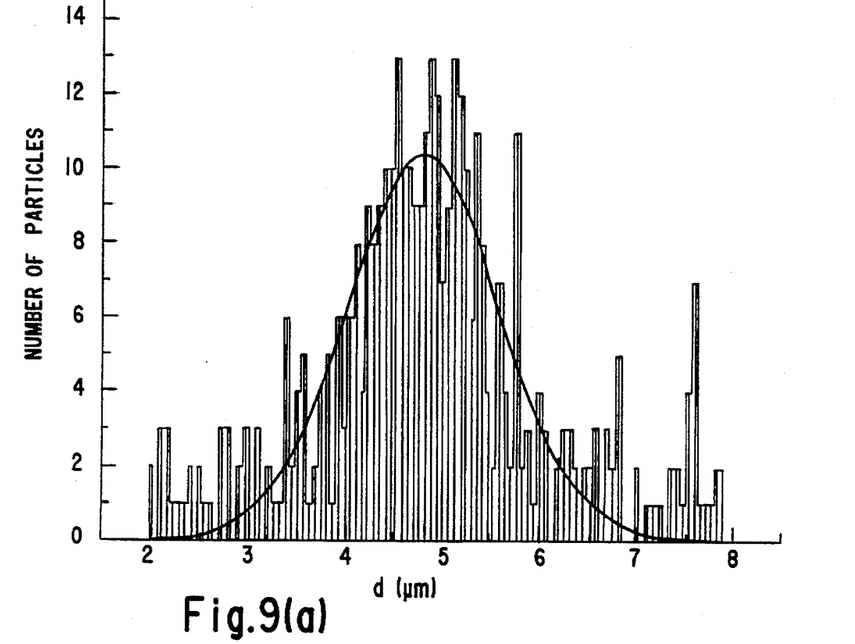
Figure 9B:
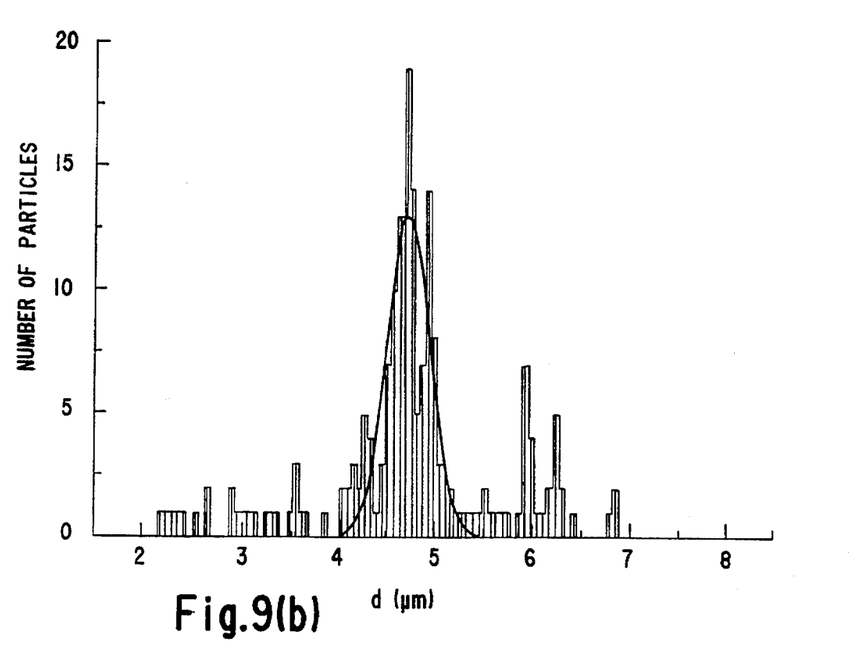

We used Equation 2 to determine the size distribution of these particles. The size distribution of *Penicillium levitum* spores generated from the LSP's of 398 individual spores using the FLSI method is presented in FIG. 9a. The size distribution produced by LSP's of 188 individual spores processed with the Mie fitting method is presented in FIG. 9b. The distribution parameters were obtained from the Gaussian distribution fitting, and gave a mean value of 4.80±0.16 µm (95% confidence interval here and below) and a standard deviation of 1.58 µm with the FLSI method, and a mean value of 4.74±0.06 µm and a standard deviation of 0.44 µm with the Mie fitting method.

Figure 10A:
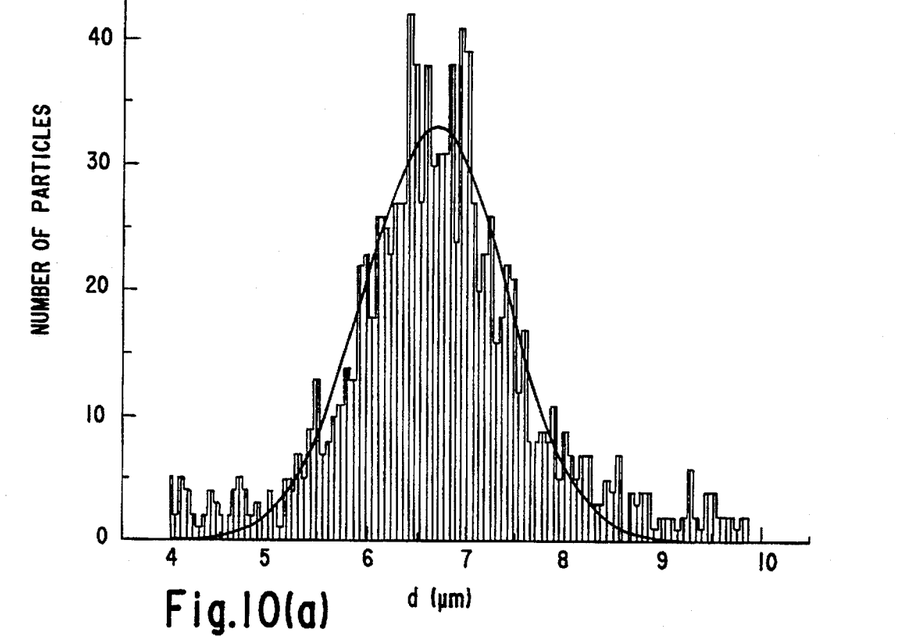
Figure 10B:
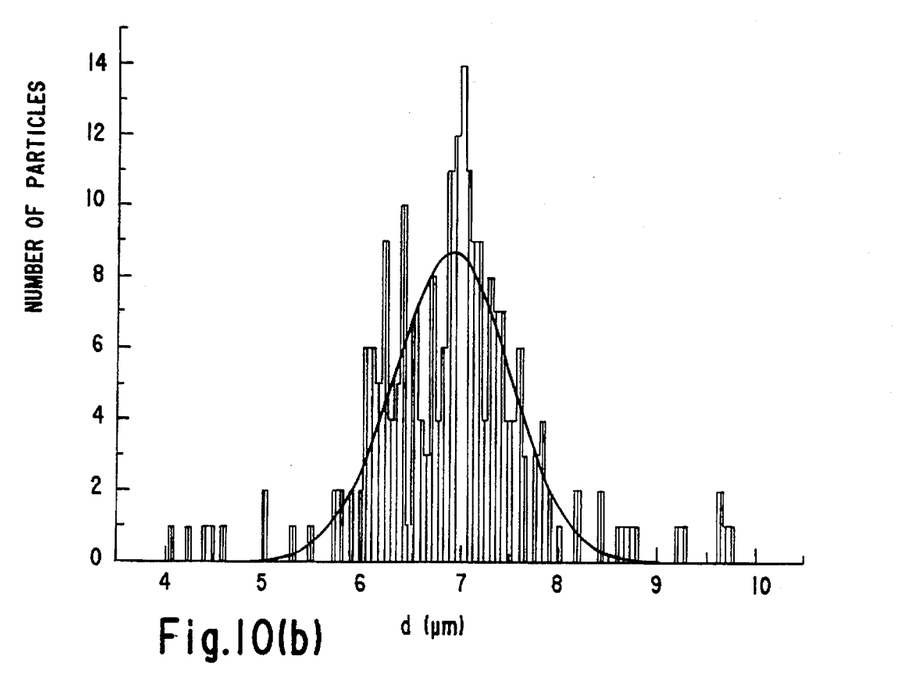

The size distribution of *Aspergillus pseudoglaucus* spores generated from the LSP's of 1097 individual spores using the FLSI method is presented in FIG. 10a. The size distribution produced by LSP's of 228 individual spores processed with the Mie fitting method is presented in FIG. 10b. The parameters of the distribution have been obtained from the Gaussian distribution fitting and showed a mean value of 6.68±0.09 µm and a standard deviation of 1.44 µm with the FLSI method, and a mean value of 6.91±0.15 µm and standard deviation of 1.17 µm with the Mie fitting method.

The size distribution parameters of the spores are in accordance with known data presented in the literature, and are as follows: size from 4 µm to 6 µm for *Penicillium levitum* and from 5.5 µm to 7.5 µm for *Aspergillus pseudoglaucus*.

Figures 11A, 11B:
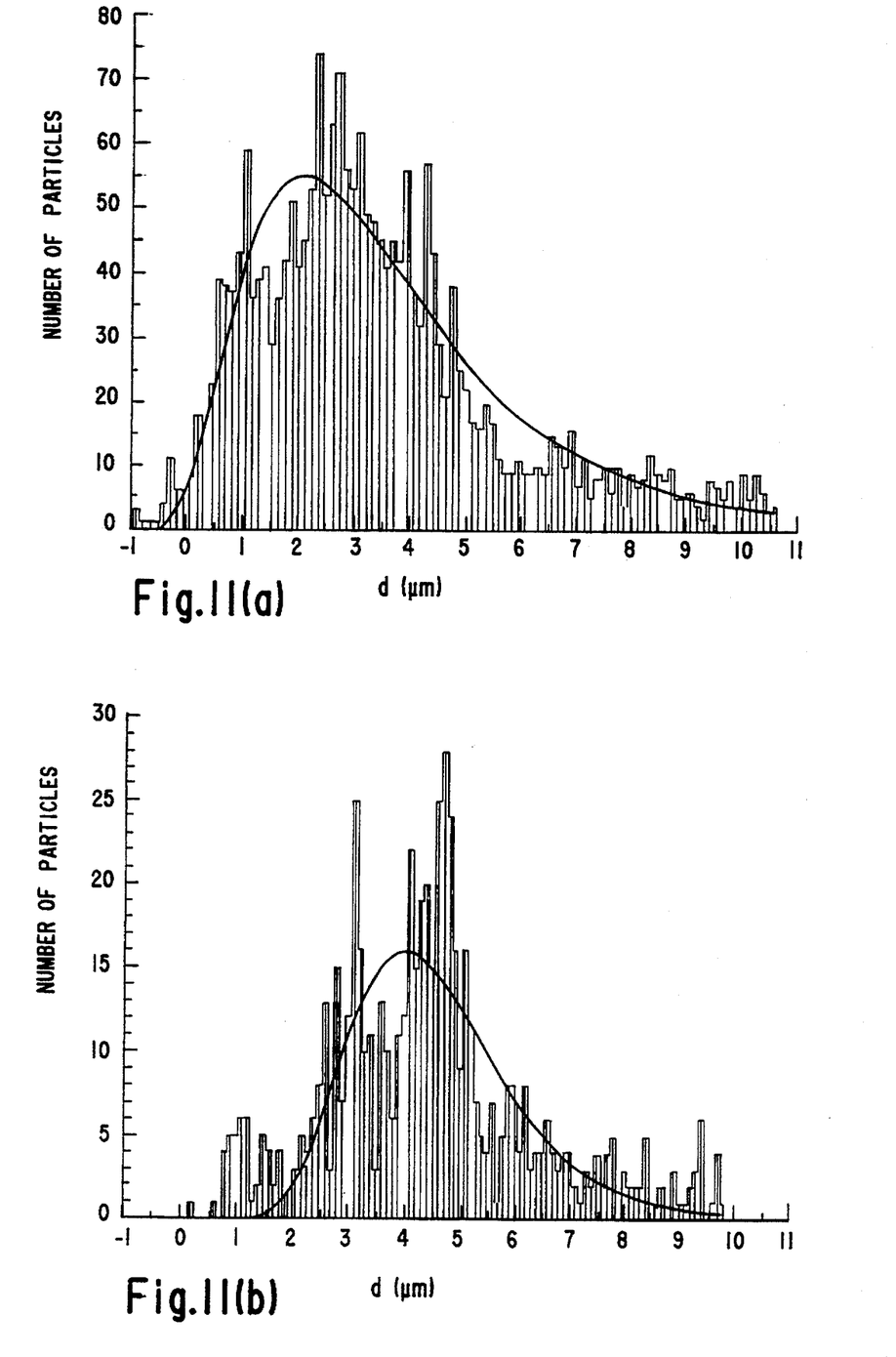

The size distribution of milk fat particles generated from LSP's of 2203 milk fat particles using the FLSI method is presented in FIG. 11a. The size distribution produced by LSP's of 610 milk fat particles processed with the Mie fitting method is presented in FIG. 11b. The distribution parameters have been obtained from the Lognormal distribution fitting and they showed the expected size of 4.02 µm and standard deviation of 2.06 µm with the FLSI method, and the expected size of 4.74 µm and standard deviation 1.65 µm with the Mie fitting method. The differences in the particle size distribution of milk fat created by the FLSI and Mie fitting methods are a subject of further research.

FLSI method can be used for for analysis of the fat content in natural milk. As usual, the size of milk fat particles are distributed between 1 and 10 µm with a maximum about at 3 µm. The size of protein micelles ranges from 0.01 µm to 0.2 µm that is under the threshold of the trigger channel of SFC. Concentration of bacterial cells is more than three orders of magnitude lower in than the concentration of fat particles. A sample of fresh raw milk was diluted by factor of $1.11 \cdot 10^4$ with water to provide suitable concentration of fat particles for the analysis with SFC. The internal flow rate was $1.003 \cdot 10^{-4}$ ml per sec.

Approximately 1000 particles were measured for each sample. The value of the size and the mass was calculated for each particle on line as well as the total weight of the particles in each sample. The measurements were repeated for same samples seven times and the results of the measurements are shown in Table 1.

The fat content was 3.93% with standard deviation of 0.34% (absolute) when 1000 particles were measured. The precision of determination of the mean value was 0.13% (absolute). The precision can be improved with increasing the total number of particles in one sample. An important advantage of the FLSI method in determination of the fat contents in milk is the absolute determination without need of chemical calibration of the instrument. The conventional methods for fat determination are based on IR-spectroscopy or turbidimetry and these methods require a homogenized sample.

TABLE 1

| Sample no | Sample weight g | Total weight of fat particles g | Fat content % |
|---|---|---|---|
| 1 | 1.172E-2 | 3.795E-8 | 3.59 |
| 2 | 1.178E-2 | 3.751E-8 | 3.53 |
| 3 | 1.160E-2 | 4.152E-8 | 3.97 |
| 4 | 1.164E-2 | 3.842E-8 | 3.63 |
| 5 | 1.167E-2 | 4.433E-8 | 4.22 |
| 6 | 1.176E-2 | 4.429E-8 | 4.18 |
| 7 | 1.175E-2 | 4.622E-8 | 4.37 |
| mean value | | | 3.93 |

This invention provides an improved method and device for rapid measurement of the size of individual microparticles in the size range from 1 μm to 12 μm. The microparticles can be latex microparticles or biological particles. The use of empirical equations included in the FLSI method enables real-time sizing of particles in absolute terms without the need for calibrating electronic and optics tracks of the device with standard particles as it is the need in case of an ordinary flow cytometer. FLSI device can be combined with a automatic particle sorter which is based on the use of electrostatic deflector for rejecting the particles of certain sizes to two separate test tubes. The electrostatic deflector is controlled by the computer after calculating out the size of the particle which normally does not take longer than a millisecond.

A specialist in the field appreciates that the different applications of the said invention may vary within the scope of the claims to be presented in the following section. It will be appreciated that the methods of the present invention can be incorporated in the form of a variety of embodiments, only a few of which are disclosed herein. It will be apparent to the expert that other embodiments exist and do not depart from the spirit of the invention. Thus, the described embodiments are illustrative and should not be construed as restrictive.

Scheme 1

$$d(\mu m) = p_1 + p_2 \times [\Delta_2(20)]^{-1} + p_3 \times [\Delta_2(20)]^{-3} \quad \text{Equation 1.}$$

$$d(\mu m) = p_1 + p_2 \times [\Delta_2(15)]^{-1} + p_3 \times [\Delta_2(15)]^{-5} + p_4 \times [\Delta_2(15)]^{-6} \quad \text{Equation 2.}$$

-continued
Scheme 1

$$T = \left( \frac{T_1}{\|T_1\|}, \frac{T_2}{\|T_2\|}, \ldots \frac{T_n}{\|T_n\|} \right)^T \quad \text{Equation 3.}$$

$$P_i = T_i \cdot \frac{M^T}{\|M\|} \quad \text{Equation 4.}$$

$$P = (P_1, P_2, \ldots P_n)^T \quad \text{Equation 5.}$$

$$V_i = \left( \frac{T_i}{\|T_i\|} - \frac{M^T}{\|M_i\|} \right) \cdot \left( \frac{T_i}{\|T_i\|} - \frac{M^T}{\|M_i\|} \right) \quad \text{Equation 6.}$$

$$v = (v_1, v_2, \ldots v_n)^T \quad \text{Equation 7.}$$

$$\rho_i = \frac{S^2_{T_iM}}{S_{T_i}S_M} \quad \text{Equation 8.}$$

$$\rho = (\rho_1, \rho_2, \ldots \rho_n)^T \quad \text{Equation 9.}$$

We claim:

1. A device for determining the size and refractive index of individual microparticles contained within a liquid sample, comprising in operational relationship:
    a laser capable of emitting a laser beam along an axis,
    a capillary flow channel placed in coaxial relationship with said laser in said axis,
    a spherical reflector having an optical axis in coaxial relationship with said capillary flow channel,
    a lens,
    a pinhole, and
    a photodetector,
arranged such that in operation laser light impinges upon individual microparticles in the capillary flow channel and is scattered onto said spherical reflector, which reflects the laser light to said lens, which focusses the reflected laser light through the pinhole onto said photodetector.

2. The device of claim 1, further comprising a plane reflector such that in operation laser light impinges upon individual microparticles in the capillary flow channel and is scattered onto said spherical reflector, which reflects the laser light to said plane reflector and lens, which focusses the reflected laser light through the pinhole onto said photodetector.

3. A method for determining the size and refractive index of individual microparticles contained within a liquid sample, comprising:
    providing a laser capable of emitting a laser beam along an axis, a capillary flow channel in coaxial relationship with said laser in said axis, a spherical reflector having an optical axis in coaxial relationship with said capillary flow channel, a lens, a pinhole, and a photodetector,
    placing a liquid sample containing microparticles in said capillary flow channel;
    illuminating said liquid sample with light from said laser;
    focussing the light scattered by said microparticles onto said photodetector by means of said spherical reflector, said lens and said pinhole,
    measuring the scattered light intensity at different angles at different times such that minima and maxima of a scattering pattern of the microparticles are recorded.

4. The method of claim 3, further providing a plane reflector such that light reflected by said spherical reflector is reflected onto said plane reflector and reflected therefrom on said lens.

5. The method according to claim 3 wherein the absolute values of diameter and refractive index of individual microparticles are calculated from their light scattering patterns using an empirical equation derived from statistical analysis of angular scattering patterns or from direct comparison of the theoretical and the experimental light scattering patterns using dot product, simple correlation, Pearson's correlation or neural network methods.

* * * * *